(12) United States Patent
Evalle

(10) Patent No.: US 6,555,333 B1
(45) Date of Patent: Apr. 29, 2003

(54) BROAD SPECTRUM FASTIDIOUS ORGANISM CULTURE MEDIUM

(75) Inventor: Minda Evalle, West Linn, OR (US)

(73) Assignee: PML Microbiologicals, Inc., Wilsonville, OR (US)

( * ) Notice: Subject to any disclaimer, the term of this patent is extended or adjusted under 35 U.S.C. 154(b) by 0 days.

(21) Appl. No.: 10/146,018

(22) Filed: May 14, 2002

(51) Int. Cl.[7] .............................. C12Q 1/04; C12Q 1/18; C12Q 1/54
(52) U.S. Cl. .............................. 435/34; 435/32; 435/14
(58) Field of Search .............................. 435/34, 32, 14

(56) References Cited

U.S. PATENT DOCUMENTS 3,781,192 A * 12/1973 Wood et al. .................. 435/6
4,177,199 A * 12/1979 Granatek et al. ........... 424/290
5,162,229 A * 11/1992 Thorpe et al. .............. 435/291

OTHER PUBLICATIONS

NCCLS Bulletin M2–A7 Performance Standards for Antimicrobial Disk Susceptibility Tests; Approved Standard (7th Ed Jan. 2000).

* cited by examiner

Primary Examiner—Louise N. Leary
(74) Attorney, Agent, or Firm—Chernoff, Vilhauer, McClung & Stenzel, LLP

(57) ABSTRACT

A culture medium suitable for Disk Susceptibility testing of a variety of fastidious microorganisms is disclosed.

7 Claims, No Drawings

BROAD SPECTRUM FASTIDIOUS ORGANISM CULTURE MEDIUM

BACKGROUND OF THE INVENTION

The use of antimicrobial therapy to treat bacterial infections and diseases in humans and animals is well known throughout the world. Successful therapy requires selection of an antimicrobial agent that is specific to the bacteria causing the infection or disease. This antimicrobial agent selection is typically made by the health practitioner with the assistance and input of clinical microbiological laboratories which can measure the in vitro susceptibility of bacteria to antimicrobial agents by a variety of methods.

In many such laboratories a standard method of assessing the susceptibility of common pathogens to antimicrobial agents is by agar disk diffusion, commonly known as Disk Susceptibility testing, whereby a disk impregnated with an antimicrobial agent is pressed onto agar that has been infused with the suspected pathogen that has been isolated from a specimen taken from the patient, the agar is incubated and microbial growth or inhibition around the disk is observed and recorded. The National Committee for Clinical Laboratory Standards (NCCLS) has formulated specific uniform methods for such Disk Susceptibility testing, criteria for quality control testing and tables for quantitatively measuring the degree of pathogenic bacteria inhibition. See "Performance Standards for Antimicrobial Disk Susceptibility Tests; Approved Standard-Seventh Edition," NCCLS Bulletin M2-A7 (January 2000).

Many common pathogens are "fastidious" microorganisms in the sense of requiring a special culture medium and a controlled environment to grow. The NCCLS Bulletin recommends the use of a Gonococcal (GC) agar medium supplemented by a 1% defined growth supplement for Disk Susceptibility testing of the fastidious microorganism *N. gonnorrhoeae*. See NCCLS Bulletin M2-A7 at page 10 and Jones et al., 27 *J. Clin. Microbiology* 2758 (1989). However such a supplemented GC agar medium was not recommended for use with any other fastidious microorganisms. The NCCLS Bulletin recommends that a variety of culture media having different formulations be used to test fastidious microorganisms such as Haemophilus species, *N. gonorrhoeae, Streptococcus pneumoniae, Streptococcus viridans* and β-hemolytic Streptocci. Ibid, page 9. This requires the preparation of a different culture medium for each suspected pathogen, a cumbersome and time-consuming task when, as is usually the case, the identify of the pathogen is unknown.

There is therefore a need in the art for a single culture medium suitable for antimicrobial Disk Susceptibility testing for multiple fastidious microorganisms and even simultaneous testing for such microorganisms.

BRIEF SUMMARY OF THE INVENTION

The foregoing need is met by the present invention, which provides a culture medium suitable for simultaneous antimicrobial Disk Susceptibility testing of multiple fastidious microorganisms, including Haemophilus species, *Streptococcus pneumoniae, Streptococcus viridans* species, β-hemolytic Streptocci, Neisseria species and Campylobacter species.

DETAILED DESCRIPTION OF PREFERRED EMBODIMENTS

The present invention lies in the discovery that the further supplementation of a particular known supplemented GC agar medium provides a culture medium useful in Disk Susceptibility testing for multiple fastidious pathogenic microorganisms.

The known supplemented GC agar medium (hereafter referred to as "base GC medium") comprises a mixture of deionized water, agar, peptones, beef and yeast extracts, starch, glucose and phosphate buffer components. More specifically the non-aqueous portion of this base GC medium comprises the components noted below present in the amounts noted:

| component | wt % (±5%) |
|---|---|
| agar | 30 |
| casein peptone | 15 |
| meat peptone | 8 |
| proteose peptone | 5 |
| peptonized milk | 4 |
| beef extract | 3 |
| yeast extract | 3 |
| starch | 3 |
| glucose | 1 |
| NaCl | 14 |
| $K_2PO_4$ | 10 |
| $KH_2PO_4$ | 2 |
| $Na_2CO_3$ | 1 |

The foregoing non-aqueous portion is preferably mixed with deionized water in a concentration of about 40 g/L of water.

The deionized water may have a pH of 5 to 7, preferably 7, since the final pH of the culture medium of the present invention is preferably 7.3±0.1 at ambient temperature; its bacteriological purity should be less than 100 CFU/mL with a TOC content of less than about 712 ppb and a resistivity of ≧2 megohms.cm at 25° C. The agar used in the base GC medium is preferably of the Iber type derived from Gelidium seaweeds that is of pharmaceutical grade, commercially available from DMV International Nutritionals of Fraser, N.Y. (hereafter "DMV").

The remaining components of the base GC medium and their commercial availability is as follows: casein peptone, a pancreatic digest of the complex of milk proteins known by that name, available as Product No. CE90-M from DMV; meat peptone, an enzymatic digest of animal tissue that is preferably a 50/50 mixture (w/w) of Product No. 102, available from Global and Product No. AE80M, available from DMV; proteose peptone, available as Product No. PP90M from DMV; peptonized milk, available as Product No. 5X59048 from Quest International Co. of Norwich, New York; beef extract, available in powder form as Product No. 150 from Global BioIngredients of Tampa, Fla. (hereafter "Global"); yeast extract, available as Product No. 151 from Global; starch (preferably reagent grade potato starch) available as Product No. S-123 from Pfanstiehl Laboratories, Inc. of Chicago, Ill.; and glucose, available as Product No. DE140 from Spectrum Laboratory Products, Inc. of Gardena, Calif. (hereafter "Spectrum"). The remaining chemical components of NaCl, $K_2HPO_4$, $KH_2PO_4$ and $Na_2CO_3$ are readily commercially available from many sources, and are preferably of ACS reagent grade.

Further supplementation of the foregoing base GC medium with a multi-component amino acid supplement and with laked horse blood allows its use for antimicrobial Disk Susceptibility testing for at least six classes of fastidious microorganisms, including Neisseria species, Haemophilus species, *Streptococcus pneumoniae, Streptococcus viridans* species, β-hemolytic Streptocci and Campylobacter species.

The amino acid component comprises deionized water and L-cysteine HCl, L-cystine, L-glutamine, guanine HCl, thiamine HCl, p-aminobenzoic acid (PABA), vitamin B12, cocarboxylase, nicotinamide adenine dinucleotide (NAD); adenine, glucose, HCl and $Fe(NO_3)_3 \cdot 9H_2O$ (ferric nitrate nonahydrate).

In a preferred formulation the amino acid component comprises an aqueous solution of the following components in the following approximate concentrations

| component | concentration |
|---|---|
| L-cysteine HCl | 26 g/L |
| L-cystine | 1 g/L |
| L-glutamine | 10 g/L |
| guanine HCl | .03 g/L |
| thiamine HCl | .003 g/L |
| PABA | .01 g/L |
| vitamin B12 | .01 g/L |
| cocarboxylase | 0.1 g/L |
| NAD | .25 g/L |
| adenine | 1 g/L |
| glucose | 100 g/L |
| $Fe(NO_3)_3 \cdot 9H_2O$ | .02 g/L |
| HCl(12N) | 5 mL/L |

The non-aqueous components of the above amino acid component are commercially available as follows.

| Component | Product No. | Source |
|---|---|---|
| L-cysteine HCl | CY115 | Spectrum |
| L-cystine | CY120 | Spectrum |
| L-glutamine | GL136 | Spectrum |
| guanine HCl | G6377 | Sigma (St. Louis, MO) |
| thiamine HCl | T4625 | Sigma Chemical Co. |
| PABA | AM150 | Spectrum |
| vitamin B12 | CY105 | Spectrum |
| cocarboxylase | C8754 | Sigma |
| NAD | N1102 | Spectrum |
| adenine | 0183 | Amresco, Inc. (Solon, OH) |
| glucose | DE140 | Spectrum |
| $Fe(NO_3)_3 \cdot 9H_2O$ | F1030 | Spectrum |

The amino acid component is preferably prepared by adding the L-cysteine HCl and L-cystine components to the deionized water in powdered form and stirring while adding the 12N HCl until the two powdered components are dissolved. The guanine HCl is added to the resulting solution and stirred for about 30 minutes until the same is dissolved. The remaining amino acid component ingredients are then added and the solution stirred until all components are in solution. The solution is then filtered with a 0.2 micron filter into a container that has been autoclaved at 127° C. for at least 30 minutes.

The laked horse blood component preferably comprises lysed red blood cells extracted from defibrinated horse blood. A preferred method of lysing and extraction is to conduct three freeze/thaw cycles on the blood, followed by centrifuging at about 1200 rpm for about 20 minutes so as to separate white blood cells and red blood cell wall fragments. Following centrifugation, the resulting laked horse blood component is preferably filtered and added to the amino acid component-supplemented base GC medium in an amount sufficient to achieve a concentration of about 30 mL/L of water present in the base GC medium.

The base GC medium is preferably formulated by preparing the non-aqueous components in a dry powder form by first combining the agar, casein peptone, starch, glucose, peptonized milk and the chemicals in, for example, a Fitzmill grinder, then placing this mixture into a blender. The meat peptone, proteose peptone, beef extract and yeast extract components are then placed in the same blender and the entire mixture is blended for approximately two hours. The deionized water is then added and thoroughly mixed in a vessel equipped with a magnetic stirrer, pH adjusted to about 7.3 by the addition of $Na_2CO_3$, followed by autoclaving at 127° C. and 22 atm for 20 to 55 minutes, depending upon batch size. The so-prepared base GC medium is then cooled to about 55° C. and the amino acid component is added and thoroughly mixed, while allowing the mixture to further cool to about 48° C. The laked horse blood component is filtered and mixed in with the base GC medium/amino acid component mixture as the same is poured into a sterile Petri dish; filtration is preferably with a 0.2 micron filter no more than 15 minutes prior to the mixing.

EXAMPLE 1

The culture medium of the present invention was formulated in five stages: (I) preparation of the base GC medium; (II) preparation of the amino acid component; (III) preparation of the laked horse blood component; (IV) combining the products of stages (I) and (II); and (V) adding the product of stage (III) while pouring the product of stage (IV) into a sterile Petri dish.

(I) Forty-five kg of a base GC medium in powdered form was prepared by mixing 13.77 kg of Iber agar with 6.6 kg casein peptone, 1.26 kg starch, 0.63 kg glucose and 1.71 kg peptonized milk powder with the chemical components NaCl (6.26 kg), $K_2HPO_4$ (4.5 kg), $KH_2PO_4$ (1.125 kg) and $Na_2CO_3$ (0.38 kg) and mixed thoroughly in a Fitzmill Model C Comminutor for 10 minutes. This mixture was then placed in a V-blender and 3.9 kg meat peptone comprising a 50/50 (w/w) mixture of enzymatic digest of animal tissue (Product No. 102 from Global and Product No. AE80M from DMV), 2.25 kg of the proteose peptone, 1.26 kg beef extract powder and 1.26 kg of yeast extract were all added and the entire mixture blended for two hours. Thirty six g of this base composition was added to 0.9 L of deionized water, heated to 60° C. and stirred thoroughly to form the base GC medium.

(II) The amino acid component was formulated by adding 25.9 g L-cysteine HCl and L-cystine in powdered form to 1 L of cold deionized water and stirred while adding 5 mL of 12N HCl until the powdered components dissolved. Guanine HCl (0.03 g) was then added and the mixture stirred for about 30 minutes to dissolve that component. The remaining ingredients of thiamine HCl (0.003 g), PABA (13 mg), vitamin B12 (10 mg), cocarboxylase (0.1 g), NAD (0.25 g), adenine (1.0 g), L-glutamine (10 g), glucose (100 g) and $Fe(NO_3)_3 \cdot 9H_2O$ (0.02 g) were added and the solution stirred for about 10 minutes until all components were in solution. The resulting solution was then filtered by a 0.2 micron filter into a pre-autoclaved vessel. Ten mL of the so-formed amino acid component was then added to the base GC medium prepared in stage (I).

(III) One L of defibrinated fresh horse blood which had been stored at 2–8° C. in a calibrated refrigerator was placed in a quarantine freezer until frozen, then removed and allowed to thaw completely at room temperature; this process was completed three more times. The freeze/thaw cycles lysed the cell walls of the red blood cells. The so-treated blood was then centrifuged at 1200 rpm for 20 minutes to separate white blood cells and fibrous components including the cell walls of the lysed red blood cells, with the latter components being discarded. The yield was 0.5 L.

(IV) Ten mL of the amino acid component of Stage (II) was added to the base GC medium of Stage (I) to form an amino acid component-supplemented base GC medium.

(V) Thirty mL of the laked horse blood was filtered through a 0.2 micron filter immediately before adding the same to 65 mL of the amino acid component-supplemented base GC medium from stage (IV) while the latter was poured into a sterile Petri dish and mixed to form the culture medium of the invention.

EXAMPLES 2–8

The culture medium of the invention was used in both Minimum Inhibitory Concentration (MIC) testing and Bauer-Kirby Disk Susceptibility testing for the pathogenic bacteria noted in the table below with the antimicrobial agents noted therein using the protocol and standards set forth in NCCLS Bulletin No. M2-A7 and in the Supplemental Tables appendix thereto, the disclosures of which are incorporated herein by reference. The results are reported in the table.

The general procedure was as follows: pathogenic bacteria specimens were obtained from American Type Culture Collection control lots and 10 isolates were obtained from all species except Campylobacter, from which 6 isolates were obtained. Petri dishes 150 mm in diameter were autoclaved and filled with the culture medium of Example 1 and brought to room temperature. Each plate was then swab-inoculated with a suspension of one of the pathogenic bacteria equivalent to a 0.5 McFarland Standard, and then the antimicrobial-impregnated disk or antimicrobial-impregnated strip for IC measurement (Etest strip from Biodisk AB, of Solna, Sweden) were pressed into the surface of the culture medium. The plates were incubated at 35° C. for 24 hours in atmospheres containing 5–7% CO and the disk diffusion zones were measured, with the exception that plates inoculated with the Campylobacter species were placed into microaerophilic chambers from Mitsubishi Gas & Chemical Co. of Japan and incubated at 35° C. for 48 hours. The tests were conducted in duplicate for each pathogenic bacteria/antimicrobial agent combination on three batches of the culture medium of Example 1, for a total of six tests for each combination. Geometric mean MIC values and arithmetic mean values of zone diameters from the Disk Diffusion tests were calculated from the data, and are reported in the table below. For comparison, known MIC breakpoints using different known culture media are also listed in the table.

The results established that both the quality and quantity of growth on the culture medium for all seven of the fastidious microorganisms tested were consistently excellent, with both Etest strip ellipses and inhibitory zone diameters being well-defined and easier to read than with conventional reference media used to test most microorganisms/antimicrobial combinations. The MICs correlated well with zone diameter measurements. The successful testing for the Campylobacter species was particularly surprising inasmuch as no standardized test method has been reported to date.

| Organism | Antimicrobial Agent | Reported MIC Breakpoints[3] | Observed MIC Breakpoints[3] | | | Observed Disk Diff. Breakpoints[4] | | |
|---|---|---|---|---|---|---|---|---|
| | | | S | I | R | S | I | R |
| S. pneumoniae | Penicillin Bm[1] | (0.06–2) | ≦0.12 | 0.25–1 | ≧2 | — | — | — |
| | Penicillin B LRT[2] | — | ≦1 | 2 | ≧4 | — | — | — |
| | Cefotaxime-m | (0.5–2) | ≦0.5 | 1 | ≧2 | ≧28 | 26–27 | ≦25 |
| | Cefotaxime-LRT[2] | — | ≦4 | — | ≧8 | ≧24 | — | ≦23 |
| | Erythromycin | (0.25–1) | ≦0.5 | 1–32 | ≧64 | ≧24 | 9–23 | ≦8 |
| | Tetracycline | (2–8) | ≦1 | 2–4 | ≧8 | ≧23 | 14–22 | ≦13 |
| | TMP/SMX | (0.5–4) | ≦1 | 2 | ≧4 | ≧13 | 11–12 | ≦10 |
| Viridans streptococci | Penicillin | (0.12–4) | ≦1 | 2 | ≧4 | ≧24 | 20–23 | ≦19 |
| | Cefotaxime | (0.5–2) | ≦£4 | — | ≧8 | ≧24 | — | ≦23 |
| | Erythromycin | (0.25–1) | ≦0.5 | 1–32 | ≧64 | ≧24 | 9–23 | ≦8 |
| | Tetracycline | (2–8) | ≦1 | 2–4 | ≧8 | ≧23 | 18–22 | ≦17 |
| | TMP/SMX | | ≦1 | — | ≧2 | ≧14 | — | ≦13 |
| β-hemolytic streptococci | Penicillin | (0.12–4) | 0.12 | — | — | — | — | ≦26 |
| | Erythromicin | (0.25–1) | ≦0.5 | 1–32 | ≧64 | ≧21 | — | ≦8 |
| Neisseria gonorrhoeae | Penicillin | (0.06–2) | ≦0.06 | 0.12–1 | ≧2 | ≧2 | 24–38 | ≦23 |
| | Ciprofloxacin | (0.06–1) | ≦0.06 | 0.12–0.5 | ≧1 | ≧35 | 25–34 | ≦24 |
| Neisseria meningitides | Penicillin | — | ≦0.12 | 0.25 | ≧0.5 | ≧26 | 24–25 | ≦23 |
| | TMP/SMX | — | ≦0.5 | 1–2 | ≧4 | ≧17 | 12–16 | ≦11 |
| Haemophilus influenzae | Ampicillin | (1–4) | ≦4 | 8 | ≧16 | ≧17 | 13–16 | ≦12 |
| | Chloramphenicol | (2–8) | ≦2 | 4 | ≧8 | ≧25 | 20–24 | ≦19 |
| | Tetracycline | (2–8) | ≦2 | 4 | ≧8 | ≧25 | 19–24 | ≦20 |
| | TMP/SMX | (0.5–4) | ≦0.5 | 1–2 | ≧4 | ≧17 | 13–16 | ≦12 |
| Campylobacter species | Erythromycin | — | ≦4 | — | ≧8 | ≧21 | — | ≦20 |
| | Ciprofloxacin | — | ≦0.5 | 1–2 | ≧4 | ≧27 | 19–26 | ≦18 |

[1]Bm = meningitis
[2]LRT = Lower Respiratory Tract
[3]μg/mL
[4]mm
S= susceptible
I= intermediate
R=resistant The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A culture medium for testing multiple fastidious microorganisms comprising (a) a base composition, (b) an amino acid component and (c) laked horse blood wherein said base composition (a) comprises deionized water and the following components present in the following approximate weight percentages:

| component | wt % (±5%) |
|---|---|
| agar | 30 |
| casein peptone | 15 |
| meat peptone | 8 |
| proteose peptone | 5 |
| peptonized milk | 4 |
| beef extract | 3 |
| yeast extract | 3 |
| starch | 3 |
| glucose | 1 |
| NaCl | 14 |
| $K_2HPO_4$ | 10 |
| $KH_2PO_4$ | 2 |
| $Na_2CO_3$ | 1; and | said amino acid component (b) comprises deionized water and L-cysteine HCl, L-cystine, L-glutamine, guanine HCl, thiamine HCl, p-aminobenzoic acid, vitamin B12, cocarboxylase, nicotinamide adenine dinucleotide; adenine, glucose, HCl and $Fe(NO_3)_3 \cdot 9H_2O$.

2. The culture medium of claim 1 wherein said laked horse blood (c) comprises lysed red blood cells.

3. The culture medium of claim 2 wherein the concentration of said lysed red blood cells is approximately 30 mL/L of deionized water.

4. The culture medium of claim 1 wherein said amino acid component (b) comprises an aqueous solution of the following components in the following approximate concentrations:

| component | concentration ± 1% |
|---|---|
| L-cysteine HCl | 26 g/L |
| L-cystine | 1 g/L |
| L-glutamine | 10 g/L |
| guanine HCl | .03 g/L |
| thiamine HCl | .003 g/L |
| p-aminobenzoic acid | .01 g/L |
| vitamin B12 | .01 g/L |
| cocarboxylase | 0.1 g/L |
| nicotinamide adenine dinucleotide | .25 g/L |
| adenine | 1 g/L |
| glucose | 100 g/L |
| $Fe(NO_3)_3 \cdot 9H_2O$ | .02 g/L |
| HCl(12N) | 5 mL/L |

5. The culture medium of claim 4 wherein said amino acid component is present in a concentration of approximately 10 mL/L of deionized water.

6. The culture medium of any of claims 1–5 in a sterile container.

7. The culture medium of claim 6 wherein said sterile container is a Petri dish.

* * * * *

UNITED STATES PATENT AND TRADEMARK OFFICE
CERTIFICATE OF CORRECTION

PATENT NO.   : 6,555,333 B1
DATED        : April 29, 2003
INVENTOR(S)  : Evalle

It is certified that error appears in the above-identified patent and that said Letters Patent is hereby corrected as shown below:

<u>Column 1,</u>
Line 14, italicize "in vitro".
Line 48, delete "identify" and insert -- identity --.
Lines 59-62, italicize "Haemophilus", "Streptocci", Neisseria" and "Campylobacter".

<u>Column 2,</u>
Line 35, italicize "Geridium".
Lines 64-66, italicize "Haemophilus", "Streptocci", Neisseria" and "Campylobacter".

<u>Column 3,</u>
Line 3, italicize "p" before "aminobenzoic".
Line 9, insert -- +1% -- after "approximate concentrations".

<u>Column 5,</u>
Line 30, italicize "Campylobacter".

<u>Columns 5/6,</u>
(In chart) 15 lines down from "S. pneumoniae", after "streptococci", correct the spelling of "Erythromicin" to -- Erythromycin --.

<u>Column 6,</u>
Line 9, insert subscript 2 after "CO" so that it reads -- $CO_2$ --.
Lines 10 and 30, italicize "Campylobacter".

<u>Column 7,</u>
Line 33, italicize "p" before "aminobenzoic".

UNITED STATES PATENT AND TRADEMARK OFFICE
CERTIFICATE OF CORRECTION

PATENT NO.    : 6,555,333 B1
DATED         : April 29, 2003
INVENTOR(S)   : Evalle It is certified that error appears in the above-identified patent and that said Letters Patent is hereby corrected as shown below:

<u>Column 8,</u>
Line 48, italicize "p" before "aminobenzoic".

Signed and Sealed this

Twenty-first Day of October, 2003

JAMES E. ROGAN
*Director of the United States Patent and Trademark Office*